United States Patent [19]

Williams et al.

[11] Patent Number: 5,456,902
[45] Date of Patent: Oct. 10, 1995

[54] DENTAL COMPOSITIONS WITH ZINC AND BICARBONATE SALTS

[75] Inventors: David R. Williams, Monroe; Christine W. Ryles, Milford; Stephen R. Barrow, Trumbull, all of Conn.

[73] Assignee: Chesebrough-Pond's USA Co., Division of Conopco, Inc., Greenwich, Conn.

[21] Appl. No.: 300,838

[22] Filed: Sep. 2, 1994

Related U.S. Application Data

[62] Division of Ser. No. 116,094, Sep. 2, 1993, Pat. No. 5,372,803.

[51] Int. Cl.$^6$ .................................................. A61K 7/18
[52] U.S. Cl. ................... 424/49; 424/53; 424/52; 424/55
[58] Field of Search ................. 424/53, 49, 52, 424/55

[56] References Cited

U.S. PATENT DOCUMENTS

| | | | |
|---|---|---|---|
| 3,935,305 | 1/1976 | Delaney et al. | 424/49 |
| 3,937,803 | 2/1976 | Delaney et al. | 424/49 |
| 3,937,804 | 2/1976 | Delaney et al. | 424/52 |
| 3,943,240 | 3/1976 | Delaney et al. | 424/49 |
| 4,022,880 | 5/1977 | Vinson et al. | 424/49 |
| 4,160,022 | 7/1979 | Delaney et al. | 424/52 |
| 4,226,851 | 10/1980 | Sompayrac | 424/53 |
| 4,528,180 | 7/1985 | Schaeffer | 424/52 |
| 4,547,362 | 10/1985 | Winston et al. | 424/49 |
| 4,575,457 | 3/1986 | Mazarin | 424/52 |
| 4,623,536 | 11/1986 | Winston et al. | 424/49 |
| 4,647,452 | 3/1987 | Ritchey et al. | 424/54 |
| 4,687,663 | 8/1987 | Schaeffer | 424/52 |
| 4,814,163 | 3/1989 | Barth | 424/49 |
| 4,814,164 | 3/1989 | Barth et al. | 424/49 |
| 4,849,213 | 7/1989 | Schaeffer | 424/53 |
| 4,943,429 | 7/1990 | Winston et al. | 424/52 |
| 5,037,633 | 8/1991 | Ziemkiewicz et al. | 424/49 |
| 5,037,634 | 8/1991 | Williams et al. | 424/49 |
| 5,085,853 | 2/1992 | Williams et al. | 424/53 |
| 5,104,644 | 4/1992 | Douglas | 424/53 |
| 5,385,727 | 1/1995 | Winston et al. | 424/49 |

*Primary Examiner*—Raymond Henley, III
*Assistant Examiner*—Keith MacMillan
*Attorney, Agent, or Firm*—Milton L. Honig

[57] ABSTRACT

A dental product is provided in a dual-compartment dispenser that includes a first and second composition in respective compartments thereof. The first composition includes a zinc salt while the second composition includes a bicarbonate salt. Preferably the first composition also contains a peroxygen compound or a $C_2$–$C_{20}$ carboxylic acid. The zinc salt in combination with the bicarbonate salt achieves an enhanced antitartar effect.

14 Claims, No Drawings ns filed Sep. 2, 1993 now U.S. Pat. No. 5,372,803.

BACKGROUND OF THE INVENTION

1. Field of the Invention

The invention concerns a dental composition and method for controlling radar formation on teeth.

2. The Related Art

Baking soda, chemically known as sodium bicarbonate, has become a popular ingredient in dental compositions. A considerable body of literature describes sodium bicarbonate dentifrices. These include U.S. Pat. Nos. 3,935,305, 3,937,803, 3,937,321, 3,937,804, 3,943,240 and 4,160,022, all to Delaney et al assigned to the Further patents in this area include U.S. Pat. Nos. 4,547,362, 4,623,536 and 4,943,429, all to Winston et al, assigned to the Church & Dwight Company, which markets Arm & Hammer brand toothpaste.

Sodium bicarbonate toothpastes such as the Arm & Hammer brand have become commercially successful because of association of the featured ingredient with malodor reduction and antibacterial activity. Whether these perceived effects are real is subject to debate. However, there is evidence to suggest that baking soda does not have antitartar activity.

Oral compositions containing both sodium bicarbonate and a peroxide have been acclaimed by the dental profession, especially through the work of Keyes. See Keyes et al. "Periodontics and Oral Hygiene", January 1978, pages 51–56.

There is a storage stability problem in formulating the products containing the two key elements of the Keyes technology. Decomposition occurs unless unusual measures are taken to separate the components. A quite successful approach to the problem has involved physical segregation of the peroxide into a compartment separate from the bicarbonate. U.S. Pat. Nos. 4,849,213, 4,687,663 and 4,528,180, all to Schaeffer, disclose a package with a dual-compartment respectively storing a peroxide gel and a bicarbonate paste. A successful commercial product known as Mentadent® has utilized the dual-compartment package concept to provide consumers with a storage stable product. Technology utilized in this product is reported in U.S. Pat. Nos. 5,12137,633 and 5,037,634, both to Williams et al. While this product has been found to have a modest level of antitartar activity, there remains room for significant improvement.

Zinc compounds, especially zinc citrate, have a long history of use as antitartar actives. In the United States, zinc citrate has been formulated into the Close-Up® and Aim® brand products by Chesebrough-Pond's. Typical of the zinc antiplaque and antitartar technology is that described in U.S. Pat. Nos. 4,022,880 (Vinson et al), U.S. Pat. No. 4,647,452 (Ritchey et al) and U.S. Pat. No. 5, 104,644 (Douglas). While zinc-formulated toothpastes have clinically demonstrated tartar reduction performance, they are generally no more effective than the commercially more prevalent pyrophosphate based technology. Taste problems limit use of higher zinc levels which would be expected to improve performance. There have been no successful attempts to combine zinc salts with bicarbonate to achieve any stable products. Our own experiments have demonstrated that zinc salts rapidly decompose bicarbonate.

Accordingly, it is an object of the present invention to provide dental compositions with improved antitartar activity.

It is another object of the present invention to provide a dental composition incorporating sodium bicarbonate in a product that exhibits significant antitartar activity while being storage stable.

It is a still further objective of the present invention to provide a dental composition incorporating sodium bicarbonate that exhibits improved antitartar activity yet minimizes taste problems often associated with antitartar actives.

These and other objects of the present invention will become more readily apparent upon consideration of the more detailed description and Examples which follow.

SUMMARY OF THE INVENTION

A dental product in a dual compartment dispenser is provided which includes:

(i) a first compartment containing a first composition that includes from about 0.1 to about 10% by weight of a zinc salt in a pharmaceutically acceptable carrier; and (ii) a second compartment containing a second composition that includes from about 0.5 to about 80% by weight of a bicarbonate salt in a pharmaceutically acceptable carrier.

In a preferred embodiment, the first composition can also include a peroxygen compound and a fluoride source to provide anticaries protection. Another embodiment utilizes ascorbic or citric acids in place of the peroxygen compound.

DETAILED DESCRIPTION

Now it has been discovered that a combination of zinc and bicarbonate salts deliver a very potent tartar inhibitory effect. It has further been established that such effect requires the zinc and bicarbonate salts to be separately packaged prior to their introduction into the oral cavity. A dual-compartment dispenser into which the respective actives are placed provides a suitable vehicle for delivery of the combined zinc and bicarbonate compositions.

Thus, as a first essential component there is required a salt delivering zinc ions. By the term "zinc ion" is meant that the zinc-atom portion of a molecule of the zinc compound in the solid or undissociated state, is capable of being dissociated into simple or complex zinc ions, especially when dispersed in an aqueous medium. Examples of the compounds that may be employed are zinc salts of the following inorganic ions: borate, bromide, carbonate, hexofluorosilicate, pyrophosphate, silicate, sulphate and titanate. Organic anions are those having from 2 to 22 carbon atoms with a charged group selected from carboxylate, sulphonate, sulphate and phosphate. Specific examples include, but are not limited to, acetate, benzoate, citrate, glycinate, lactate, phenolsulphonate, salicylate, tartrate, acetylacetonate, maleate, succinate, ascorbate, and gluconate. Most preferred is zinc citrate, which may be in hydrated form.

The zinc salts will generally be present in the dental compositions of the present invention in an amount from about 0.05 to about 10%, preferably between about 0.2 and 5%, optimally between about 0.8 and 3% by weight.

Oral compositions of the present invention may be in the form of either a toothpaste, gel or mouthwash.

The term "pharmaceutically acceptable carrier" will include such functional ingredients as water, humectants, abrasives, thickeners and surfactants. Total levels of these material may range anywhere from about 20 to about 99% by weight.

The first composition, i.e. the composition with zinc salt, preferably is a gel. Advantageously, the gel will include a peroxygen compound such as hydrogen peroxide, urea peroxide, calcium peroxide and the salts of perborate, persilicate, perphosphate and percarbonate. The most suitable for this invention is hydrogen peroxide. The amount of the peroxygen compound may range from about 0.1 to about 10% by weight. In terms of active weight hydrogen peroxide, the amount will range from about 0.5 to about 5%, preferably from about 0.8 to about 4%, optimally between about 1 and 3% by weight.

Instead of the peroxygen compounds, the first composition may contain a $C_2$-$C_{20}$ carboxylic acid. Illustrative acids include citric, malic, lactic and ascorbic acids. Levels of the acids may range in amounts similar to that of the peroxygen compound, i.e. from about 0.1 to about 10% by weight. Citric acid is most preferred. When present, these acids will either be in gel or paste type compositions.

Advantageously, the pH of the first composition will be held between about 3.2 and 5.0, preferably from 4.0 to 4.5.

Another important component of the first composition is that of a fluoride anticaries compound. Illustrative of fluoride compounds are sodium fluoride, potassium fluoride, calcium fluoride, magnesium fluoride, stannous fluoride, stannous monofluorophosphate, sodium monofluorophosphate and copper fluoride. These sources should release anywhere from about 25 to 3500 ppm of fluoride ion. The anticaries agent will be present in an amount from about 0.01 to about 5%, preferably from about 0.1 to about 2.5%, optimally between about 0.2 and about 1.5% by weight of the peroxide composition.

Water may be present in the compositions in amounts ranging from about 20 to about 95% by weight. When the peroxide composition is a gel, the amount of water may range from about 30 to about 55%, optimally between about 35 and 45% by weight.

Structurants are necessary where the first composition is in the form of a gel. Most suitable as the structurant are the polyoxyethylene-polyoxypropylene copolymers where the hydrophobic portion, represented by ($C_3H_6O$), has a molecular weight ranging from about 2,750 to 4,000 and the hydrophilic portion, represented by ($C_2H_4O$), constitutes about 70 to 80% of the weight of the copolymer. Commercially the copolymers are available from the BASF Corporation under the trademark, Pluronic® F88, F99, F108 and F127. Most preferred is Pluronic® F127 (hereinafter referred to by its CTFA name, Poloxamer 407®) which has a molecular weight ranging from about 10,000 to 15,000, and containing about 70% of the hydrophilic polyoxyethylene moiety. Amounts of the copolymer can range anywhere from 18 to 25% by weight, preferably between 19 and 24%. Poloxamers are particularly suitable for this invention because of their wide pH tolerance, good compatibility with hydrogen peroxide and unique gel properties.

Glycerol is another preferred ingredient of the first composition when in gel or rinse form. Amounts of glycerol may range from about 5 to about 50%, preferably between about 5 to about 20% by weight for the rinse but preferably between about 35 and 45% by weight for the gel.

Adjunct minor ingredients may also be present in the composition of this invention. Included may be small amounts of colorant, flavor and antioxidant.

Oral compositions of the present invention will include, besides a first composition, an additional separate bicarbonate-containing second composition, each held within a separate container available for simultaneous delivery in substantially equal volumes for use in the mouth.

The bicarbonate second composition will also contain a fluoride anticaries compound selected from the same fluoride compounds in essentially identical amounts to those described hereinabove with respect to the first composition. Especially preferred is sodium fluoride. Bicarbonate salts will be present in alkali metal form, examples of which are sodium and potassium. Typically, the concentration of bicarbonate salt will range from about 0.5 to about 80%, preferably from about 5 to about 50%, optimally between about 8 and about 20% by weight of the total combined dental product. The pH of the bicarbonate composition may range from about 7.0 to about 9.5, most preferably about 8.0 to 9.0. When the bicarbonate composition is in toothpaste or gel form, there will typically be included a natural or synthetic thickening agent in an amount from about 0.1 to 10%, preferably about 0.5 to 5% by weight. Thickeners may include hydroxypropyl methyl cellulose, hydroxyethyl cellulose, sodium carboxymethyl cellulose, xanthan gum, tragacanth gum, karaya gum, arabic gum, Irish moss, starch, alginates and carrageenans.

Surfactants are normally also included in the bicarbonate compositions. These surfactants may be of the anionic, nonionic, cationic or amphoteric type. Most preferred are sodium lauryl sulfate, sodium dodecylbenzene sulfonate and sodium laurylsarcosinate. Surfactants are usually present in an amount from about 0.5 to about 5% by weight.

When in the form of a toothpaste or gel, the bicarbonate compositions will normally include an abrasive in addition to the bicarbonate. Abrasives may be selected from water-insoluble alkali or alkaline earth metal salts of metaphosphate (IMP), calcium carbonate, aluminate and silicate. Especially preferred are silica, dicalcium phosphate and calcium carbonate. Amounts of the abrasive will range from about 5 to about 80% by weight.

Flavors are usually present in both the first and, when suitable, second compositions. These flavors may be based on oils of spearmint and peppermint. Examples of other flavoring materials include menthol, clove, wintergreen, eucalyptus and aniseed. Flavors may range in concentration from about 0.1 to about 5% by weight of the total composition.

Sweetening agents such as saccharin, sodium cyclamate, aspartame, sucrose and the like may be included at levels from about 0.1 to about 5% by weight of the total composition.

Other additives may also be incorporated into the oral compositions including preservatives, silicones, other synthetic or natural polymers such as Gantrez S-97®, and antigingivitis actives.

Relative weight amounts of the first composition to that of the second composition will range from about 1:2 to 2:1, preferably about 1:1. Each component may be kept isolated in a separate compartment of a dispenser. Advantageously, the dispenser will simultaneously deliver approximately equal amounts of each composition through an orifice at whose end the separate compositions may intermingle. Suitable for this purpose are dual-compartment packages such as described in the Schaeffer patents, U.S. Pat. Nos. 4,528,180 and 4,849,213. Most preferred is where the first composition is in the form of a transparent gel and the second composition is in the form of an opaque paste.

The following examples will more fully illustrate the embodiments of this invention. All parts, percentages and proportions referred to herein and in the appended claims are by weight of the total composition unless otherwise stated.

EXAMPLE 1

Typical of the present invention is a peroxide gel composition whose formulation is detailed under Table I. The formulation of Table I may be utilized in combination with a bicarbonate composition detailed under Table II each of the compositions being held in a separate compartment of a dual-compartment dispenser.

TABLE I

Peroxide Gel Component

| Ingredient | Wt. % |
| --- | --- |
| Pluronic F127 | 20.000 |
| Glycerin | 40.000 |
| Hydrogen Peroxide (35% food grade) | 4.285 |
| Zinc Citrate | 4.000 |
| Methyl Salicylate | 0.500 |
| Sodium Fluoride | 0.240 |
| Phosphoric Acid (85% w/w) | 0.150 |
| FD&C Blue 1 | 0.005 |
| Deionized water | Balance |

TABLE II

Bicarbonate Paste Component

| Ingredient | Wt. % |
| --- | --- |
| Polyol II (sorbitol and other sugars) | 48.710 |
| Syloid 63XX (abrasive silica) | 15.000 |
| Sodium Bicarbonate | 10.000 |
| PEG 32 (polyethylene glycol) | 5.000 |
| Sylox 15x (thickening silica) | 4.600 |
| Sodium Lauryl Sulfate | 2.980 |
| SD Alcohol 38B | 2.850 |
| Cellulose Gum | 0.800 |
| Menthol | 0.500 |
| Sodium Saccharin | 0.500 |
| Titanium Dioxide | 0.300 |
| Sodium Fluoride | 0.230 |
| Deionized water | Balance |

EXAMPLE 2

A clinical trial was conducted to compare the dental product of Example 1 with an identical product that did not include zinc citrate. Procter & Gamble's product known as Crest® Tartar Control was used as a reference; the latter product is a typical paste formulation containing pyrophosphates as the antitartar agent.

Protocol for the clinical was as follows. Six panelists participated in the study. These panelists were carefully selected to meet a long list of criteria such as exhibiting visible tartar within only 1 to 2 months of a professional cleaning. Tartar present on the lingual aspect of the 6 interior Mandibular teeth was evaluated according to the Volpe/Manhold Scoring Index. Following an initial tartar assessment, each panelist received a thorough dental cleaning. Panelists were then given either Pepsodent® or Aim® toothpaste for use over the following 3 weeks to allow tartar to build. Another tartar evaluation identified the baseline for a panelist's normal tartar growth rate. A second dental prophylaxis was then performed to remove dental tartar, rendering the panelists ready to receive the first test product (Example 1 with zinc citrate). Tartar evaluations were then conducted after 2 and 3 weeks of product usage. Pepsodent®/Aim® were then given to the panelists for a 4 week washout period.

The Mandibular interior teeth were then scaled to remove tartar buildup over the washout period. Panelists were next assigned to use Crest® Tartar Control toothpaste for the subsequent 3 weeks. Evaluations were again conducted at the 2 and 3 week period. In a further phase of the test, the panelists were directed to use Pepsodent®/Aim® for another 4 week washout. Again, the Mandibular interior teeth were scaled to remove tartar buildup over the 4 week washout period. Panelists were then assigned to Example 1 without zinc citrate for the next 3 weeks. Tartar evaluations were conducted at the 2 and 3 week interval.

Results of the tests are reported in Table III below.

TABLE III

Clinical Test Results

| Product | % Reduction in Tartar |
| --- | --- |
| Crest ® Tartar Control | 36 |
| Example 1 (without zinc citrate) | 20 |
| Example 1 (with zinc citrate) | 69 |

From the results of Table III, it can be seen that inclusion of zinc citrate provided a surprisingly large improvement in antitartar activity within the context of a sodium bicarbonate dual-compartment product.

The foregoing description and Examples illustrate selected embodiments of the present invention. In light thereof, various modifications will be suggested to one skilled in the art, all of which are within the spirit and purview of this invention.

What is claimed is:

1. A dental product in a dual compartment dispenser comprising:
   (i) a first compartment containing a first composition that includes from about 0.1 to about 10% by weight of a zinc salt in a pharmaceutically acceptable carrier; and
   (ii) a second compartment containing a second composition that includes from about 0.5 to about 80% by weight of a bicarbonate salt in a pharmaceutically acceptable carrier.

2. A product according to claim 1 wherein the zinc salt is zinc citrate.

3. A product according to claim 1 wherein the first composition has a pH ranging from 3.2 to 5.0.

4. A product according to claim 1 wherein the relative weight ratio of the first composition to the second composition ranges from about 1:2 to 2:1.

5. A method for inhibiting the formation of tartar on teeth, the method comprising:
   (i) extruding a first composition onto a toothbrush, the first composition comprising from about 0.1 to about 10% by weight of a zinc salt in a pharmaceutically acceptable carrier;
   (ii) extruding a second composition onto the toothbrush comprising from about 1 to about 80% by weight of a bicarbonate salt in a pharmaceutically acceptable carrier; and
   (iii) brushing the teeth simultaneously with a combination of the first and second compositions.

6. A method according to claim 5 wherein the first and second compositions are extruded simultaneously onto the toothbrush.

7. A method according to claim 5 wherein the first and second compositions are extruded nonsimultaneously onto the toothbrush.

8. A method according to claim 5 further comprising maintain pH in a range from 3.2 to 5.0

9. A product according to claim 1 wherein the zinc salt is formed with inorganic anions selected from the group consisting of borate, bromide, carbonate, hexofluorosilicate, pyrophosphate, silicate, sulphate and titanate.

10. A product according to claim 1 wherein the zinc salt is formed with organic anions having from 2 to 22 carbon atoms and a charged group selected from the group consisting of carboxylate, sulphonate, sulphate and phosphate.

11. A product according to claim 1 wherein the zinc salt is selected from the group consisting of zinc acetate, zinc benzoate, zinc citrate, zinc glycinate, zinc lactate, zinc phenolsulphonate, zinc salicylate, zinc tartrate, zinc acetylacetonate, zinc maleate, zinc succinate, zinc ascorbate and zinc gluconate.

12. A method according to claim 5 wherein the zinc salt is formed with inorganic anions selected from the group consisting of borate, bromide, carbonate, hexofluorosilicate, pyrophosphate, silicate, sulphate and titanate.

13. A method according to claim 5 wherein the zinc salt is formed with organic anions having from 2 to 22 carbon atoms and a charged group selected from the group consisting of carboxylate, sulphonate, sulphate and phosphate.

14. A method according to claim 5 wherein the zinc salt is selected from the group consisting of zinc acetate, zinc benzoate, zinc citrate, zinc glycinate, zinc lactate, zinc phenolsulphonate, zinc salicylate, zinc tartrate, zinc acetylacetonate, zinc maleate, zinc succinate, zinc ascorbate and zinc gluconate.

* * * * *